United States Patent [19]
Xavier

[11] Patent Number: 5,119,832
[45] Date of Patent: Jun. 9, 1992

[54] EPIDURAL CATHETER WITH NERVE STIMULATORS

[76] Inventor: Ravi Xavier, 732 Ibis Way, N. Palm Beach, Fla. 33408

[21] Appl. No.: 493,966

[22] Filed: Mar. 15, 1990

Related U.S. Application Data

[63] Continuation-in-part of Ser. No. 378,324, Jul. 11, 1989, which is a continuation-in-part of Ser. No. 294,380, Jan. 6, 1989, abandoned.

[51] Int. Cl.⁵ ...................... A61N 1/04; A61M 25/00
[52] U.S. Cl. .................................. 128/786; 128/642; 604/49; 604/51
[58] Field of Search ...................... 128/786, 898, 642; 604/48, 49, 51

[56] References Cited

U.S. PATENT DOCUMENTS

| | | |
|---|---|---|
| 3,734,094 | 5/1973 | Calinog . |
| 4,073,287 | 2/1978 | Bradley et al. . |
| 4,285,347 | 8/1981 | Hess ................................ 128/786 |
| 4,294,245 | 10/1981 | Bussey ................................ 604/20 |
| 4,360,031 | 11/1982 | White ................................ 128/786 |
| 4,379,462 | 4/1983 | Borkan et al. . |
| 4,411,648 | 10/1983 | Davis et al. . |
| 4,512,351 | 4/1985 | Pohndorf .......................... 128/786 |
| 4,549,556 | 10/1985 | Tarjan et al. . |
| 4,699,147 | 10/1987 | Chilson et al. . |
| 4,699,157 | 10/1987 | Shonk . |
| 4,744,371 | 5/1988 | Harris ................................ 128/786 |
| 4,777,955 | 10/1988 | Brayton et al. . |
| 4,784,156 | 11/1988 | Garg . |
| 4,787,892 | 11/1988 | Rosenberg . |
| 4,917,670 | 4/1990 | Hurley et al. .................. 604/51 |

FOREIGN PATENT DOCUMENTS

| | | | |
|---|---|---|---|
| 3602219 | 7/1987 | Fed. Rep. of Germany ...... 128/784 |
| 1005796 | 3/1983 | U.S.S.R. ............................. 128/786 |
| 2124503 | 2/1984 | United Kingdom .................. 604/51 |

*Primary Examiner*—Kyle L. Howell
*Assistant Examiner*—K. M. Pfaffle
*Attorney, Agent, or Firm*—Kenneth W. Iles

[57] ABSTRACT

A catheter intended to be temporarily implanted in the epidural spaces of a person for relief of pain includes four circumferential ring electrodes connected to terminals by fine wires embedded in the side wall of the catheter for attachment to a conventional pulse generator and a hollow elongated body with an injection portal at the proximal end and an aperture at the distal end for continuously administering a pain-relieving agent in a liquid form. The agent may be a narcotic or anesthesia. Methods for treating pain using the catheter include electrical stimulation, the use of narcotics, or anesthesia, which can be administered in any order, or simultaneously as empirically determined to provide the best pain relief for each patient.

11 Claims, 1 Drawing Sheet

EPIDURAL CATHETER WITH NERVE STIMULATORS

REFERENCE TO RELATED APPLICATION

This application is a continuation-in-part of application Ser. No. 378,324, filed Jul. 11, 1989, now pending, which is a continuation-in-part of application Ser. No. 294,380, filed Jan. 6, 1989, now abandoned.

BACKGROUND OF THE INVENTION

1. Field of the Invention

The present invention is directed to catheter electrodes for the relief of pain. More particularly, the present invention is directed to a catheter for electrical stimulation of the epidural space and administration of local anesthetics.

2. Description of Related Art

Electrical stimulation of the spinal column through electrodes implanted in the epidural spaces has been found useful in controlling pain. The use of injected anesthetics or narcotics has been found useful in the temporary relief of pain. In some instances, the local anesthetic or the narcotic is administered into the epidural spaces along the spinal column. These and other techniques are used to control intra-operative pain, post-operative pain, and chronic pain states. Such techniques as currently practiced, however, leave many patients without satisfactory pain relief.

This is a result of the characteristics of the modalities for pain control and of the nerves that carry pain impulses. The nerve fibers carrying pain impulses to the spinal cord are classified into three major groups according to their speeds of conduction. Type A nerve fibers carry pain impulses at the rate of about thirty to one hundred-twenty meters per second. Type B nerve fibers carry pain impulses at the rate of about five to fifteen meters per second. Type C nerves carry pain impulses most slowly of all, about 0.1 to two meters per second. These fibers all relay impulses through an area in the spinal cord called the substantial gelatinosa. From this site, the nerve fibers are projected to the brain. The three primary modalities for pain control and their primary disadvantages are as follows.

First, local anesthetics may be injected. Local anesthetics act by blocking the transmission of pain impulses in types A, B and C nerve fibers. Local anesthetics typically, however, relieve pain only a relatively short time and if large amounts are injected into the epidural spaces to achieve longer term pain relief, the local anesthetic is absorbed into the blood stream and leads to local anesthetic toxicity. Consequently, typical anesthetics must be administered every hour or two.

Second, narcotics, such as morphine sulfate, or methadone, may be injected into the epidural spaces. Narcotics act by modulating the impulse transmission at the substantial gelatinosa. Narcotics are, however, extremely dangerous and may well spread upwards into the brain and lead to the arrest of breathing, and to death. Narcotics typically bring pain relief within from about twelve minutes to about twenty-five minutes and provide continuous pain relief for six to about eighteen hours, depending on the particular narcotic used and the type of pain being treated. Because narcotics may be extremely addictive, physicians generally prefer to use non-narcotic pain relievers whenever possible.

Third, an optimal amount of electrical stimulation of the spinal cord through the epidural spaces is used to relieve pain, but acts almost exclusively on the pain impulse traffic along the type C fibers in the spinal nerves, leading to only a 50%-60% reduction in pain. This well-established modality is used in the treatment of pain from chronic inflammation, and chronic pain from cancer, old injuries, nerve injuries, and so forth and can be permanently implanted, complete with its own subcutaneous power supply, for example Trojan et al U.S. Pat. No. 4,549,556. Although it is useful for many patients, electrical epidural nerve stimulation does not lead to full, or even satisfactory pain relief in many other patients.

In addition, in the case of an injected pain-relieving agent, whether local anesthetics or narcotics, the drugs quickly relieve pain but their pain killing ability dissipates over time due to absorption of the pain reliever by the body, which metabolizes the agent. Thus, the pain-relieving agent must be administered periodically and frequently. Typically, either local anesthetics or narcotics are administered every two to six hours (although some narcotics may provide pain relief for up to about eighteen hours in some cases). This regimen requires the regular attendance by a trained medical worker who must monitor the patient's pain, the dosage and timing of the injections, and then repeatedly administer the drug. This process is labor intensive. Even more importantly, it results in wide undulations in the level of pain experienced by the patient. When the anesthetic or narcotic is first administered, nearly all the pain vanishes. With the passage of time, however, the pain returns before the next dose is given. If doses are spaced closely enough to prevent the recurrence of pain, overdosing the patient is quite likely.

During operations, anesthesia must be administered through a different method than is used to control post-operative pain. In some cases, even in a hospital, overdoses of narcotics lead to the death of patients.

Thus, it is clear that the prior art of pain relief includes some significant disadvantages.

Therefore, a need exists for a device and a method that achieve effective full-time satisfactory relief from serious pain; that reduce the likelihood of an overdose of an anesthetic or narcotic; and permit application of a uniform dosage across time; and that permits the physician to establish anesthesia for surgery as well as to control post-operative pain.

SUMMARY OF THE INVENTION

Accordingly, it is a primary object of the present invention to provide a device and method for achieving effective and satisfactory relief from severe pain.

It is a further object of the present invention to provide such a device that reduces the likelihood of an overdose of an anesthetic or narcotic.

It is a further object of the present invention to provide a device that can be used to establish anesthesia during the operation as well as to reduce post-operative pain.

These and other objects of the present invention are achieved by providing a catheter comprising an elongated hollow body or lumen having a distal end and a proximal end with a first opening in the distal end and a second opening in the proximal end, at least four ring electrodes equally spaced downwardly from the distal end and a wire connecting each of the four electrodes to a separate terminal. In a preferred embodiment, the wires are separately embedded in the side wall of the elongated hollow body. The electrodes are silver or platinum and the wires are stainless steel. The proximal end of the elongated hollow body or lumen, includes an injection portal which is adapted to receive in sealing engagement by frictional attachment means a conventional syringe (for example, a Luer-Lok ® threaded fitting). The injection portal deviates away from the longitudinal axis of the elongated hollow body, as does an electrode casing for holding the wires and keeping them free from the catheter itself.

The device is inserted through the skin a distance of about ten to fifteen cm to lie in the epidural spaces, with the rest of the apparatus left protruding from the patient. The catheter is preferably about ninety centimeters long and about seventeen to nineteen gauge outside diameter. The device is inserted in the patient through a larger needle by well known conventional techniques.

The elongated hollow body may be made from any convenient durable flexible and physiologically inert material such as a polyurethane or medical grade silicon, and preferably is made from a substantially inert low-friction substance such as polytetrafluoroethylene (hereinafter "PTFE") (Teflon ® non-stick material). Use of such material prevents interaction of the bodily fluids with the catheter itself. In addition, it is important for the catheter to be radiopaque so that an X-ray picture will show any parts of the catheter that may inadvertently remain in the patient after the catheter is removed.

In use, electricity is pulsed through two of the terminals, and hence through two of the ring-electrodes that are connected to form a complete electrical circuit, and the patient's epidural spaces, where it relieves pain in the type C nerves. Concurrently, a pain-relieving agent such as an anesthetic or narcotic, may be injected through the lumen. In another method of application, an intravenous-type solution feed bottle is attached to the injection portal, allowing a steady slow flow of a dilute solution of a pain-relieving agent through the lumen and into the epidural spaces, where the agent acts to relieve pain transmitted by all three types of nerves while avoiding the danger of overdose. Use of this catheter leads to pain reductions of about 95%.

Several methods for relieving pain may be employed utilizing the catheter. The lumen may be used to deliver anesthesia, anesthetic, or narcotic substances, or other pain-relieving agent. For example, a local topical anesthetic may be conventionally applied to a patient, and the catheter then implanted into the patient's epidural spaces. Then an anesthetic may be introduced through the lumen to permit painless surgery. Following surgery, the ring electrodes may be employed to use electrical stimulation for the relief of pain. The use of electrical stimulation through the electrodes to relieve pain may be used in conjunction with any anesthesia, anesthetic, or narcotic. These four basic treatment modalities of anesthesia, anesthetics, narcotics, and electrical stimulation may be used in any order or in conjunction with one another subject to accepted medical practice.

It is intended that the catheter be implanted for, at most, several days, primarily for treatment of pain during surgery and for post-operative pain.

Other objects and advantages of this invention will become apparent from the following description taken in connection with the accompanying drawings, wherein is set forth by way of illustration and example, an embodiment of this invention.

DESCRIPTION OF THE PREFERRED EMBODIMENT

Figure 1:
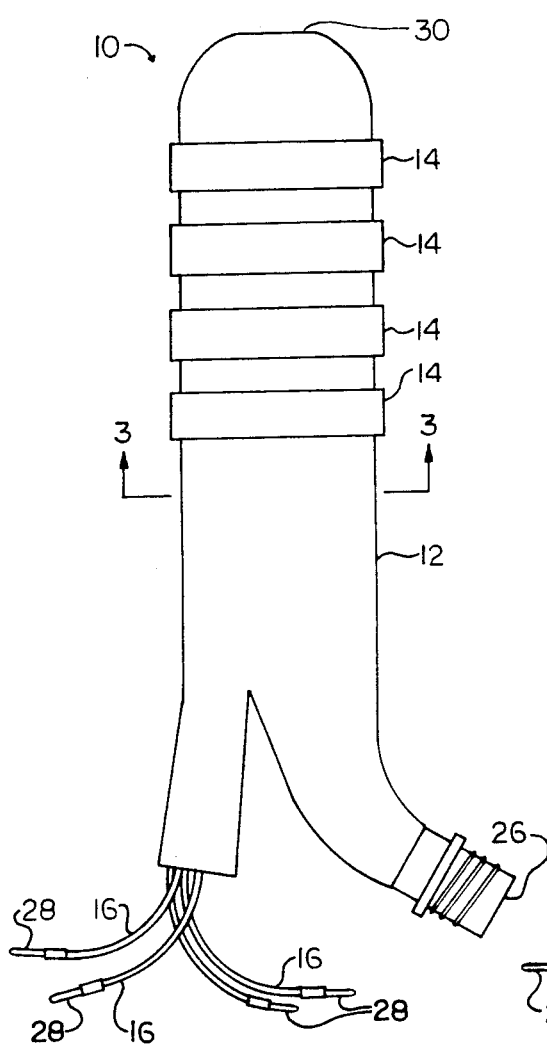
FIG. 1 is a side elevation of a catheter according to the present invention.

Referring to FIG. 1, there is shown an epidural catheter with nerve stimulators, or catheter, 10 comprising an elongated hollow tubular body 12, which incorporates two different systems for inducing anesthesia, which are: (1) electrical pulse stimulation; and (2) introduction of a pain-relieving agent into the patient's body.

Four circumferential ring electrodes 14 coat the exterior of the catheter 10. One ring electrode 14 is located approximately one centimeter from the distal end of the catheter 10 and the four ring electrodes are equally spaced from that starting point. In a preferred embodiment, the electrodes are three mm wide and about five to six mm apart. Ring electrodes 14 are made from a highly electrically conductive metal that does not react extensively with bodily fluids. Ring electrodes 14 are preferably made from silver, gold, or platinum. The ring electrodes 14 comprise an outer band which is adapted to conduct electricity into the tissues of the epidural spaces. It is important that the electrodes be smooth to prevent abrasion of the tissues during insertion and removal of the catheter 10.

The electrodes 14 may be made from an electrically-conductive metallic powder, such as silver metal precipitated in an analytical reagent mixed with an inert silicon medical adhesive. The catheter body 12 is preferably made from a physiologically inert radiopaque material such as medical grade silicon, polyurethane, or polytetrafluoroethylene (PTFE). If the catheter body 12 is not made wholly from PTFE, it may be coated with PTFE to reduce the friction upon insertion of the catheter into the patient. When the elongated hollow body 12 of the catheter 10 is made from a physiologically inert medical grade silicon elastometer, the ring electrodes 14 can be formed by adding a dispersion agent solvent, such as xylene, toluene, freon, or other silicon solvent to the mixture of powered silver and silicon medical adhesive to provide a substantially liquid mixture. The resulting mixture may be applied to the surface of the catheter 10 in the desired patterns. After the reagent solvent evaporates and the adhesive cures, the ring electrodes 14 are permanently bonded to the catheter 10. Preferably, relatively little adhesive is used, the ratio of adhesive to silver being between approximately 1:3 to 1:5 by weight. This low ratio of adhesive to silver increases the electrical conductivity of the ring electrodes 14. To actually form the ring electrodes 14, the adhesive-silver mixture is preferably wiped onto special non-stick tape, which is wound around the circumference of the elongated tubular body, or body, 12 in the desired location. The tape is removed after the adhesive has cured, leaving a ring electrode 14 securely bonded to the catheter 10. Naturally, the ring electrodes 14 must be mechanically and electrically conducted to wires for conducting a current through the ring electrodes.

One wire 16 is connected to each ring electrode 14 and threaded through separate holes 18 in the side wall of the body 12. It may be very difficult to pass the conductor wires 16 through the length of the body 12 due to the small size of the components. To make this process easier, the catheter body 12 is soaked in a hydrocarbon solvent, such as xylene, toluene, or freon, which greatly swells the catheter body 12 and the size of the holes 18, allowing the wires 16 to be pulled through the holes. The solvent also reduces the friction of the catheter body 12. An advance strand, such as nylon fish line or prolene suture (size 0) is pulled through the hole, tied to the electrode wires, which are then also pulled through the hole. After the solvent is driven off, the catheter body 12 contracts to its original size, shape and strength. Since the electrode wires 16 are separately implanted in separate lumens in the side wall of the catheter body 12, it is not necessary to insulate them within the side wall 15 of catheter body 12 and they are also protected from corrosion caused by bodily fluids. Alternatively, each wire 16 can be insulated with, e.g., PTFE, and threaded through a single lumen in the side wall of body 12, with just enough insulation stripped from the tip of each wire to make contact with ring electrodes 14.

Figure 4:
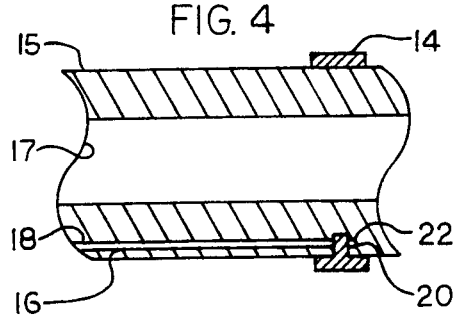
FIG. 4 is a fragmentary cross sectional view of the catheter illustrating the connection of a wire with an electrode.

Referring to FIG. 4, each ring electrode 14 is located over a small hole 20 that penetrates a portion of the tubular side wall 15 of the catheter body 12. The wire 16 is threaded through the hole 18 and is pulled through the entire length of catheter body 12 until the lead line is free from the catheter body. The lead line is then detached from the wire 16, which is pulled back through the catheter body 12 (that is, to the left as shown in FIG. 4) until the end 22 of the wire 16 lies within the hole 20. Then, the silver adhesive mixture referred to above is introduced into the hole 20 prior to formation of the ring electrode 14, thus ensuring a good mechanical and electrical bond between each wire 16 and each ring electrode 14. Other fabrication and manufacturing techniques may also be employed to make the catheter.

Figure 2:
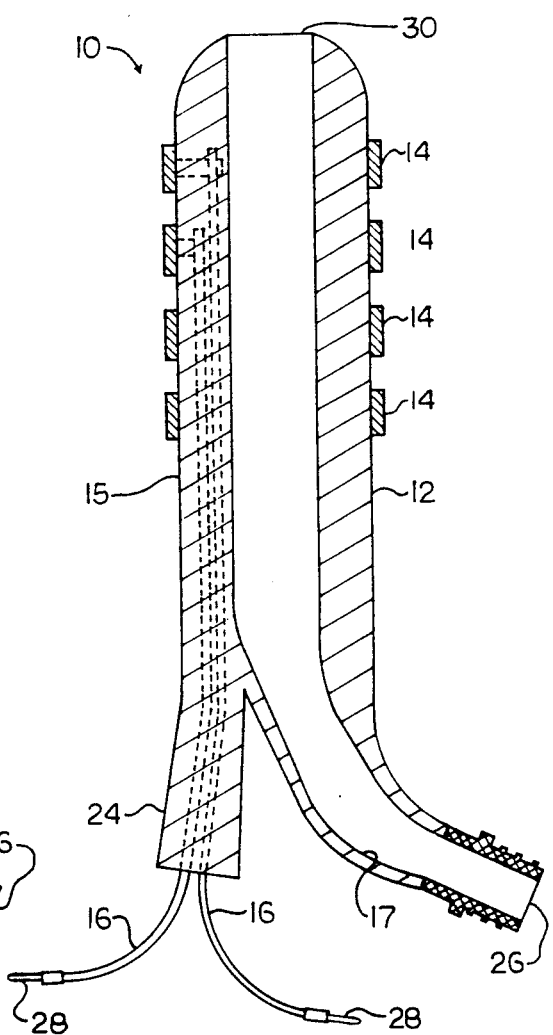
FIG. 2 is a sectional side elevation of the catheter of FIG. 1.
Figure 3:
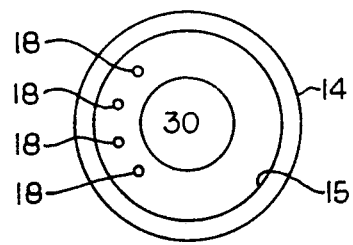
FIG. 3 is a cross section taken along lines 3—3 of FIG. 1, taken along a line such that only two of the four wires and electrodes are visible.

Referring to FIGS. 1 and 2, the proximal end of the catheter body 12 includes an electrode casing 24, which is canted to one side relative to the longitudinal axis of the catheter body 12 to protect the wires 16 and keep them physically separate from the injection portal 26, which will be discussed in detail below. Each wire 16 is connected to a terminal 28. The terminals are in turn plugged into a conventional pulse generator manufactured for easing pain through electrical stimulation. Two electrodes are used to form a complete circuit. Customarily, only two electrodes are used at the same time. The particular electrodes to be used for a given application, the voltage level, and the frequency of the pulses are all determined empirically through trial and error for each specific case. There are, however, broad ranges of frequencies and voltages that are normally effective. The voltage is typically within the range of 0.0 to 10.5 V and frequencies are typically within the range of 0-120 pulses/second.

The wires 16 extend from the bottom portion of the electrode casing 24 by about two inches (2") (5 cm), just long enough to conveniently connect them to the leads of a pulse generator 19 by plugging the four terminals 28 into the terminal block 21 of the pulse generator 19. Typically, the terminals 28 are roughly cylindrical and are adapted to be plugged directly into the receptor terminals of the pulse generator (not shown).

The wires 16 are preferably stainless steel and each wire 16 comprises a twisted bundle of about 90 strands of 12 micron wire. The wire 16 may be coated with an appropriate insulation such as PTFE, which reduces the friction during the embedding process. The wires 16 may be fixed to the terminals 28 by welding or a specialized soldering technique.

The catheter body 12 further includes an aperture 30 at its distal end for administration of an anesthetic that can be injected through the injection portal 26 at the proximate end of the catheter 10. The lengthwise tubular passage, or lumen, 17 conveys the pain-relieving agent from the injection portal 26, which is outside the patient's body, to the aperture 30 in the distal end, which is inside the patient's body. The presence of an anesthetic or narcotic solution inside the catheter body 12 makes it important that the wires 16 and ring electrodes 14 not communicate with the interior portion of catheter body 12 because some such solutions conduct electricity. The injection portal 26 is specifically adapted to receive a conventional syringe tip, or I.V. fitting by frictional engagement to prevent leaking or the introduction of air.

To use the catheter 10, it is first inserted into the epidural spaces of the patient through a larger needle by well known techniques. In use in the preferred embodiment, a dilute solution of a pain-relieving agent, such as an anesthetic or a narcotic, may be continually and gradually fed into the catheter body 12 where it provides steady and continuous pain relief when it enters the body. The pain-relieving agent is mixed with or dissolved in water, which acts as a carrier. The pain-relieving mixture or solution may also include other chemicals, such as salts. The pain-relieving agent used in the catheter 10 and the method for alleviating or relieving pain disclosed herein relies on the use of one or more liquid pain-relieving agents, whether dissolved, diluted, suspended or otherwise mixed with a carrier liquid or not. The injection portal 26 is specifically adapted to engage a threaded syringe fitting, although the injection portal 26 may be adapted to fit any desired means for administering a liquid to a patient.

The epidural catheter with nerve stimulators 10 may be employed in a variety of methods for relieving pain. In general, the electrical pulse stimulation available through the ring electrodes 14 may be used in conjunction with either narcotics or anesthetics for the general relief of pain. In the methods of using the catheter 10, electrical stimulation and pain relieving agents may be used in any order. The treatment modality that works best with each particular patient in a particular phase of treatment can be determined from empirical feedback from the patient.

In particular, the anesthetic or narcotic, or other pain-relieving agent is preferably in the liquid state. In the liquid state, the pain-relieving agent can be administered continuously in diluted form through the injection portal 26 to the aperture 30 in the distal end of the catheter 10 through the lumen 17.

Thus, one process for relieving pain in accordance with the catheter 10 is the continuous controlled dosage of a anesthetic or narcotic into the epidural spaces of the patient. Secondly, electrical stimulation of the nerves in the epidural spaces can be used to relieve pain, particularly in the type C nerve fibers of the spinal nerves, by pulsing any two of the four ring electrodes 14. Third, the electrical stimulation by the ring electrodes 14 may be employed simultaneously with the administration of a pain-relieving agent, such as a narcotic or an anesthetic. Fourth, the pain-relieving agent may be administered independently of and without electrical stimulation or prior to electrical stimulation. Fifth, electrical stimulation through the electrodes 14 may be practiced and then halted, thereafter the treatment being made with a narcotic or anesthetic on an episodic or continuous basis.

In short, methods of relieving pain that employ the catheter 10 bring a flexibility in treatment modalities to the patient that has not been present before. Even if or when electrical stimulation is no longer necessary for pain control, or does not adequately control pain, the catheter 10 may remain inside the patient's body and continue to provide a valuable pathway for the administration of other pain-relieving agents. The availability of the catheter 10 for performing this function reduces the trauma to the patient because subsequent provisions for relieving pain do not require further invasion of the patient's body, thereby reducing the risk of infection and the general discomfort to the patient. In addition, placement of the epidural catheter in the epidural spaces delivers the pain-relieving agent directly to the best possible location for the relief of pain in many types of surgery.

It is to be understood that while certain forms of this invention have been illustrated and described, it is not limited thereto, except in so far as such limitations are included in the following claims.

Having thus described the invention, what is claimed as new and desired to be secured by Letters Patent is as follows:

1. A method of pain treatment carried out in the epidural spaces of a patient comprising:
 (a) implanting a catheter into the epidural spaces of a patient, said catheter comprising means for administering a liquid pain-relieving agent to a patient further comprising an elongated hollow body having a distal end and a proximal end, a lumen therebetween, said body further comprising a first opening at said proximal end and a second opening at said distal end whereby a liquid pain-relieving agent is introduced through said first opening, flows through said lumen and out of said second opening into the patient, at lest two ring electrodes spaced downwardly from said distal end on the exterior surface of said lumen and electrically insulated from one another, a separate wire connected to each said ring electrode, each said wire being embedded in the wall of said elongated hollow body from each said electrode to said proximal end of said elongated hollow body and terminating in a separate terminal external to said lumen, and an electrical pulse generating means connected to said terminals for administering electrical pulses to said ring electrodes for pain relief in the patient;
 (b) pulsing electricity through at least two said terminals in a manner consistent with relieving pain;
 (c) continually and gradually delivering a liquid pain-relieving agent through said lumen into the epidural spaces of a patient through a delivery means connected to said proximal end of said lumen;
 (d) leaving said catheter in place in the epidural spaces of the patient for at least three days;
 thereby providing steady and continuous pain relief to the patient.

2. A method in accordance with claim 1, wherein said step (c) of delivering a liquid pain-relieving agent comprises delivering an anesthetic.

3. A method in accordance with claim 1, wherein said step (c) of delivering a liquid pain-relieving agent comprises delivering a narcotic.

4. A method in accordance with claim 1, wherein said step (c) of delivering a liquid pain-relieving agent comprises delivering an anesthesia.

5. A method in accordance with claim 1, wherein said step of delivering a pain-relieving agent further comprises the step of injecting said pain reliever into said proximal end of said lumen.

6. A method in accordance with claim 1 wherein step (c) is performed prior to performing step (b).

7. A method in accordance with claim 1 wherein steps (b) and (c) are performed simultaneously.

8. A method in accordance with claim 1 wherein said catheter comprises four ring electrodes, each of said ring electrodes connected to a separate terminal by a separate wire, said terminals being external to said lumen, and further comprising the steps of selecting two of said ring electrodes for connection to said pulse generator that provide the greatest degree of pain relief for the patient, wherein said steps (b) and (c) are performed simultaneously.

9. A method in accordance with claim 1, wherein said step of delivering a liquid pain-relieving agent further comprises a step of dripping said liquid pain-relieving agent through said lumen into the epidural spaces of a patient.

10. A method of pain treatment for chronic pain carried out in the epidural spaces of a patient comprising the sequential steps of:
 (a) implanting a catheter into the epidural spaces of a patient, said catheter comprising means for administering a liquid pain-relieving agent to a patient further comprising an elongated hollow body having a distal end and a proximal end, a lumen therebetween, said body further comprising a first opening at said proximal end and a second opening at said distal end whereby a liquid pain-relieving agent is introduced through said first opening, flows through said lumen and out of said second opening into the patient, at least two ring electrodes spaced downwardly from said distal end on the exterior surface of said lumen and electrically insulated from one another, a separate wire connected to each said ring electrode, each said wire being embedded in the wall of said elongated hollow body from each said electrode to said proximal end of said elongated hollow body and terminating in a separate terminal external to said lumen, and an electrical pulse generating means connected to said terminals for administering electrical pulses to said ring electrodes for pain relief in the patient;
 (b) continually and gradually delivering a narcotic through said lumen into the epidural spaces of a patient through a delivery means connected to said proximal end of said lumen until toxic doses of the narcotic no longer control pain effectively and a state of tolerance develops in the patient;
 (c) terminating delivery of said narcotic through said lumen when said state of tolerance has developed;
 (d) continually and gradually administering a local anesthetic through said lumen into the epidural spaces of a patient through a delivery means connected to said proximal end of said lumen until said tolerance for said narcotic disappears;

(e) pulsing electricity through at least two said terminals in a manner consistent with relieving pain simultaneously with step (d); until the tolerance of the narcotic disappears and (f) resuming delivery of said narcotic, terminating said step of pulsing electricity through said electrodes, and terminating said step of administering a local anesthetic; thereby providing steady and continuous pain relief to the patient.

11. A process in accordance with claim 10 wherein the local anesthetic administered in step (d) is a non-narcotic anesthetic.

* * * * *